(12) United States Patent
Ono et al.

(10) Patent No.: US 6,932,610 B2
(45) Date of Patent: Aug. 23, 2005

(54) PROCESS FOR PRODUCING AN ARTIFICIAL BONE MODEL AND AN ARTIFICIAL BONE MODEL PRODUCED BY THE PROCESS

(75) Inventors: Hidenori Ono, Setagaya (JP); Mamoru Suzuki, 3-43-10-1102 Honmachi, Shibuya-ku, Tokyo (JP), 151-0071

(73) Assignees: Ono & Co., Ltd., Tokyo (JP); Mamoru Suzuki, Tokyo (JP)

( * ) Notice: Subject to any disclaimer, the term of this patent is extended or adjusted under 35 U.S.C. 154(b) by 0 days.

(21) Appl. No.: 10/726,305

(22) Filed: Dec. 1, 2003

(65) Prior Publication Data

US 2004/0175686 A1 Sep. 9, 2004

(30) Foreign Application Priority Data

Dec. 2, 2002 (JP) .......................................... 2002-349914

(51) Int. Cl.[7] ................................................. G09B 23/28
(52) U.S. Cl. ......................................... 434/274; 434/267
(58) Field of Search ................................ 434/262, 267, 434/274; 424/423; 128/848; 623/16.11, 23.61, 23.56, 23.57, 23.58, 23.62

(56) References Cited

U.S. PATENT DOCUMENTS 3,787,900 A * 1/1974 McGee ........................ 424/422
4,629,464 A * 12/1986 Takata et al. ............. 623/23.61

(Continued)

FOREIGN PATENT DOCUMENTS

| DE | 100 55 465 A1 | 5/2002 |
| EP | 0 703 036 A | 3/1996 |
| JP | 6-154305 A | 6/1994 |
| JP | 2000-084943 A | 3/2000 |
| JP | 2002-067174 A | 3/2002 |
| WO | WO 92/08567 A | 5/1992 |

OTHER PUBLICATIONS

H. Furuzawa et al, "Fabrication of Ti–HAP Composite for Artificial Bone by Injection Molding", *Research Reports of the Center for Industrial Technology of Aichi Prefecture*, No. 37, pp. 70–73 (2001) (with English translation of Abstract).
K. Takahashi, "Present Status and Problems of Molded Models for Medical Use", *Preprints of the 23rd Rapid Prototyping Symposium*, pp. 31–34 and 4 sheets of illustration (2002) (English language (i) "Translation of the cover sheet"; (ii) "Translation of relevant portion of Contents"; and (iii) translation of "Outline of the preprint for the lecture cited").

*Primary Examiner*—Kurt Fernstrom
(74) *Attorney, Agent, or Firm*—Frishauf, Holtz, Goodman & Chick, P.C.

(57) ABSTRACT

A process for producing an artificial bone model in accordance with the selective laser sintering process which comprises extending a powder material for sintering comprising 30 to 90 parts by weight of powder of a synthetic resin and 10 to 70% by weight of an inorganic filler to form a thin layer and irradiating a portion of the thin layer having the shape formed based on tomograpic information of a natural bone with laser light so that the irradiated portion of the thin layer is sintered. The extension of the powder material for sintering to form the thin layer and the irradiation of the thin layer with laser light for sintering are conducted repeatedly. The artificial bone model can three-dimensionally reproduce steric shapes of natural bones such as bones in the human body precisely and accurately and exhibits the property for cutting closely similar to that of natural bones. The artificial bone model can be used for educational training or for studying a plan for curing before a surgical operation.

24 Claims, 8 Drawing Sheets

U.S. PATENT DOCUMENTS

| | | | |
|---|---|---|---|
| 4,654,464 A | * | 3/1987 | Mittelmeier et al. ......... 128/898 |
| 4,834,756 A | * | 5/1989 | Kenna ........................ 128/898 |
| 5,076,869 A | | 12/1991 | Bourell et al. |
| 5,152,791 A | * | 10/1992 | Hakamatsuka et al. .. 623/23.56 |
| 5,370,692 A | * | 12/1994 | Fink et al. .................. 128/898 |
| 5,490,962 A | | 2/1996 | Cima et al. |
| 5,634,956 A | * | 6/1997 | Suh et al. ..................... 65/33.1 |
| 5,824,084 A | * | 10/1998 | Muschler .................... 128/898 |
| 6,215,093 B1 | | 4/2001 | Meiners et al. |
| 6,231,607 B1 | * | 5/2001 | Ben-Bassat et al. ...... 623/16.11 |
| 6,537,589 B1 | * | 3/2003 | Chae et al. .................. 424/602 |
| 6,540,784 B2 | * | 4/2003 | Barlow et al. ........... 623/16.11 |
| 6,630,153 B2 | * | 10/2003 | Long et al. .................. 424/422 |
| 6,689,375 B1 | * | 2/2004 | Wahlig et al. .............. 424/426 |
| 6,692,448 B2 | * | 2/2004 | Tanaka et al. .............. 600/587 |
| 6,692,760 B2 | * | 2/2004 | Miyamoto et al. .......... 424/423 |
| 2002/0029094 A1 | | 3/2002 | Koreishi |

* cited by examiner

PROCESS FOR PRODUCING AN ARTIFICIAL BONE MODEL AND AN ARTIFICIAL BONE MODEL PRODUCED BY THE PROCESS

BACKGROUND OF THE INVENTION

1. Field of the Invention

The present invention relates to a process for producing an artificial bone model. More particularly, the present invention relates to an artificial bone model which can three-dimensionally reproduce steric shapes of natural bones such as bones in the human body precisely and accurately and exhibits the property for cutting closely similar to that of natural bones. The present invention further relates to an artificial bone model produced by the process and a use of the artificial bone model for educational training or for studying a plan for curing before a surgical operation.

2. Description of Related Art

Medical treatments accompanied with cutting of bones such as recovery of a skull having defect or deformation, treatments of auditory organs having a complicated structure of bones, surgical treatments of necrosis of caput ossis femoris and treatments of various types of complicated fracture have been conducted in wide areas such as the orthopedics, the brain surgery, the pectoral surgery, the oral surgery, the otorhinolarygology, the plastic surgery and the veterinary surgery. However, the opportunity for educational training of doctors skilled in the surgical treatments accompanied with cutting of bones is not frequent. Heretofore, as the material used for education, training and experiment in the medical field, models prepared by visually imitating the appearance of bones taken from remains of animals and human beings in accordance with artistic methods such as carving and cutting using paper, synthetic resins, wood and gypsum have generally been used. In limited cases, real bones are provided as postmortem specimens by the favor of a deceased person or the bereaved. However, it is actually difficult to obtain bones for educational, training and experimental purposes.

When a portion of a bone has a damage due to a disease or an accident, the bone is spontaneously recovered when the width of the damage is 5 mm or smaller. However, when the damage in a bone exceeds 5 mm, auto-transplantation of the bone is conducted taking a portion of a bone of the hip or a leg of the patient. However, since the size of the bone which can be taken is limited and the load to the body of the patient is great due to cutting of a healthy portion of a bone, various artificial bones have been developed and utilized. For example, as the artificial bone which is made of biologically active materials and organic polymers, has a great mechanical strength and exhibits a great biological activity, an artificial bone which is made of 30 to 90% by weight of glass powder containing CaO and $SiO_2$ as the main component and 10 to 70% by weight of a copolymer of 2,2-bis [4-(3-methacryloxy-2-hydroxypropoxy)-phenyl]propane and triethylene glycol dimethacrylate or the like is proposed (Japanese Patent Application Laid-Open No. Heisei 6(1994)-154305, page 2). As the composite material for artificial bones exhibiting excellent mechanical properties and biological compatibility, a composite material made of titanium and hydroxyapatite prepared in accordance with the metal powder injection molding process is reported (Hideo Furuzawa, Yasuhiro Kataoka and Koichi Nagata, Aichi-ken Kogyo-Gijutu Center Kenkyu Hokoku (Research Reports of the Center fo Industrial Technology of Aichi Prefecture), No. 37, 2001). An artificial bone made of titanium in accordance with the laser sintering rapid prototyping process is also reported as the artificial bone which is custom-made in accordance with the condition of the individual patient.

The above artificial bones are embedded in the living body by the surgical operation and supplements the natural bones. The properties are focused on the strength and the compatibility with the body and other properties such as the property for cutting are, in general, far different from those of natural bones. It is not necessary that the artificial bone embedded in the living body has completely the same shape as that of the natural bone since it is sufficient that the artificial bone can functionally supplement the natural bone. In general, an artificial bone has a simplified shape than that of the natural bone. Therefore, an artificial bone prepared for embedding into the living body is not suitable for the training for surgical operations.

For a shaped model for medical uses, the model should have the same shape as the natural bone including the detailed structures and have the real shape enabling manual examination of the three-dimensional structure which cannot be seen directly from the outside. A technology in which data of the steric shape of the human body are supplied to an apparatus for optically forming a shape and an artificial bone model is prepared by curing a photocurable liquid resin. (Kazuyuki Takahashi, Preprints of the 23rd Rapid Prototyping Symposium, page 31, 2002). The shape including detailed structures can be reproduced accurately when a photocurable liquid resin is used. However, since the article which are being prepared by the process cannot stand by itself during the preparation, it is necessary that a support called a supporting structure be added during the preparation and be removed manually after the preparation is completed. The cured product of the photocurable resin exhibits the property for cutting far different from that of the natural bone and is not suitable for training for the operation of cutting bones.

It is attempted that three-dimensional data are reconstructed from X-ray CT images and an artificial bone model is visually observed three-dimensionally on a display. In accordance with this method, many images of sections of the artificial bone model cut at desired portions can be displayed, and various simulations can be conducted with examination of the shapes before the operation. However, the effect of the examination on the display is limited, and it is most desirable that a plan for curing is made before the operation using a steric artificial bone model having the same shape as that of the natural bone.

SUMMARY OF THE INVENTION

The present invention has an object of providing an artificial bone model which can three-dimensionally reproduce steric shapes of natural bones such as bones in the human body precisely and accurately and exhibits the property for cutting closely similar to that of natural bones.

As the result of extensive studies by the present inventor to overcome the above problems, it was found that steric shapes of natural bones could be three-dimensionally reproduced by using a powder material for sintering comprising 30 to 90 parts by weight of powder of a synthetic resin and 10 to 70% by weight of an inorganic filler and forming the shape based on tomograpic information of natural bones by irradiation with laser light in accordance with the laser sintering rapid prototyping process. The present invention has been completed based on the knowledge.

The present invention provides:

(1) A process for producing an artificial bone model in accordance with a selective laser sintering process which comprises extending a powder material for sintering comprising 30 to 90 parts by weight of powder of a synthetic resin and 10 to 70% by weight of an inorganic filler to form a thin layer and irradiating a portion of the thin layer of the powder material for sintering in a shape formed based on tomograpic information of a natural bone with laser light so that the powder material for sintering of the irradiated portion of the thin layer is sintered, the extension of the powder material for sintering to form the thin layer and the irradiation of the portion of the thin layer with laser light for sintering being conducted repeatedly.

(2) A process according to (1), wherein the powder of a synthetic resin comprises fine particles having a spherical shape;

(3) A process according to (1) or (2), wherein the artificial bone model is used for educational training;

(4) A process according to (1) or (2), wherein the artificial bone model is used for studying a plan for curing before a surgical operation;

(5) A process according to any one of (1) to (4), wherein the average diameter of fine particles of the powder of a synthetic resin is in a range of 5 to 200 μm;

(6) A process according to any one of (1) to (5), wherein the powder of the synthetic resin is the powder of at least a resin selected from the group consisting of nylons, polycarbonates, polyesters, polyacetals, polyethylene, polypropylene, polyvinyl chloride, polystyrene, polybutylene, ABS resins, cellulose-based resins, acrylic resins, epoxy resins and fluororesins;

(7) A process according to any one of (1) to (6), wherein the powder of the synthetic resin is powder of a nylon resin;

(8) A process according to any one of (1) to (7), wherein the inorganic filler is glass beads;

(9) A process for producing an artificial bone model of radiolucent areas in human bone according to (1), wherein the CT data of the area from the tomographic information of a natural bone is reversed;

(10) An artificial bone model produced by the process described in any one of (1) to (9);

(11) Use of the artificial bone model described in (10) for educational training; and (12) Use of the artificial bone model described in (10) for studying a plan for curing before a surgical operation.

BRIEF DESCRIPTION OF THE DRAWINGS

The numbers in FIG. 1 have the meanings as listed in the following:

1: A laser
2: A galvanometer
3: A spot of laser light
4: A powder head
5: A powder material for sintering
6: A roller for supplying a powder material for sintering
7: A stage
8: An elevator
9: A part-build chamber In FIG. 4(a) and FIG. 4(b), M means malleus, P means promontory, RW means round window niche, I means incus and OW means oval window. In FIG. 5(a) and FIG. 5(b), A means anterior semicircular canal, L means lateral semicircular canal, P means posterior semicircular canal, F means vertical segment of the facial nerve and S means sigmoid sinus.

DESCRIPTION OF THE PREFERRED EMBODIMENTS

The process of the, present invention is the process for producing an artificial bone model in accordance with a process which comprises extending a powder material for sintering comprising 30 to 90% by weight of powder of a synthetic resin and 10 to 70% by weight of an inorganic filler to form a thin layer and irradiating a portion of the thin layer of the powder material for sintering in a shape based on tomographic information of a natural bone with laser light so that the powder material for sintering of the irradiated portion of the thin layer is sintered, the extension of the powder material for sintering to form the thin layer and the irradiation of the portion of the thin layer with laser light for sintering being conducted repeatedly. The word sintering originally means to bring about agglomeration in by heating in the metallurgical area. In the present invention, the term sintering is defined as the phenomena in which the powder of the synthetic resin in the material for sintering is fused by the irradiation of the laser light and the particles of the inorganic filler in the material for sintering are adhered together by the fused synthetic resin and the material for sintering within the area irradiated by the laser light is brought into a solid mass after cooling. The process set forth above is not particularly limited. For example, the process known in the art called selective laser sintering process which is explained in detail in published applications, for example, WO 92/08567 and EP 0703036, is applicable for the process of the present invention. The process for producing an artificial bone model in the present invention is referred to as a selective laser sintering process for convenience. The selective bone model has been applied to produce molded articles from plastic materials in recent areas. However, the process for molding a bone model or a bone model produced by the selective laser sintering process has not been disclosed at least with the knowledge of the inventors of the present invention. In the selective laser sintering process, the powder material for sintering is extended to form a thin layer, and a portion of the thin layer having the object shape is irradiated with a laser light or the like so that the irradiated portion of the powder material for sintering is sintered with laser light. The extension of the powder material for sintering and the sintering of the thin layer of the material with the laser light are repeated successively. The thickness of the thin layer of the powder material for sintering extended in a single step is, in general, 0.01 to 0.3 mm. The thickness can be suitably selected in accordance with the productivity of the product and the accuracy of the dimension. When the sintering of one layer of the powder material for sintering by the irradiation with laser light is completed, an elevator on which the product under preparation is placed is lowered by a thickness of one layer. Then, the powder material for sintering for the next step is extended to form a thin layer and the laser light is applied, always on a plane at the same position. The process for extending the powder material for sintering is not particularly limited. For example, the powder material for sintering may be sprayed from an upper position, or the supplied powder material for sintering may be treated by a roller to prepare a thin layer having a uniform thickness. Between the above processes, the process of treating by a roller is preferable since a thin layer having a uniform thickness and a small content of a cavity can be formed with excellent reproducibility.

In the process of the present invention, since the artificial bone model is produced in accordance with the selective laser sintering process, the artificial bone model under preparation is buried in the powder material for sintering which is not yet sintered and surrounds the artificial bone model under preparation, and no support is necessary for any desired shape of the model. Therefore, the artificial bone model having the object shape can be produced in a single stage. When the entire artificial bone model is prepared by irradiation with laser light, the artificial bone model is taken out of the powder material for sintering which is not yet sintered, and the completed artificial bone model can be obtained directly.

The powder material for sintering used in the present invention comprises 30 to 90% by weight of powder of a synthetic resin and 10 to 70% by weight of an inorganic filler and, preferably, 50 to 80% by weight of powder of a synthetic resin and 20 to 50% by weight of an inorganic filler. When the amount of the powder of a synthetic resin is less than 30% by weight and the amount of the inorganic filler exceeds 70% by weight, the obtained artificial bone model is hard and brittle, and there is the possibility that the property for cutting is different from that of the natural bone. When the amount of the powder of a synthetic resin exceeds than 90% by weight and the amount of the inorganic filler is less than 10% by weight, there is the possibility that the property for cutting of the obtained artificial bone model is poor. Since the hardness and the brittleness (or the flexibility) of the obtained artificial bone model can be adjusted by controlling the relative amounts of the powder of a synthetic resin and the inorganic filler, any artificial bone model in the range of a hard bone model of an aged person to a soft bone model of an infant can be prepared in accordance with the object.

The powder of a synthetic resin used in the present invention is not particularly limited. Examples of the synthetic resin include nylons, polycarbonates, polyesters, polyacetals, polyethylene, polypropylene, polyvinyl chloride, polystyrene, polybutylene, ABS resins, cellulose-based resins, acrylic resins, epoxy resins and fluororesins. Among these resins, nylons are preferable and nylon 11 is more preferable.

In the process of the present invention, it is preferable that the powder of a synthetic resin comprises fine particles having a spherical shape. When the fine particles of the powder of a synthetic resin has a spherical shape, a thin layer of the powder material for sintering having a uniform thickness and a small fraction of void can be formed with excellent reproducibility. The size of the fine particles of the powder of a synthetic resin is not particularly limited. It is preferable that the average diameter of the fine particles of the powder of a synthetic resin is in a range of 5 to 200 $\mu$m, more preferably in the range of 20 to 120 $\mu$m and most preferably in the range of 40 to 90 $\mu$m. Powder of a synthetic resin having an average diameter smaller than 5 $\mu$m cannot be produced easily, and there is the possibility that the cost increases. When the average diameter of the powder of a synthetic resin exceeds 200 $\mu$m, the uniformity of the obtained artificial bone model decreases, and there is the possibility that the property for cutting becomes poor.

The inorganic filler used in the present invention is not particularly limited. Examples of the inorganic filler include talc, calcium carbonate, glass beads, silica, clay, kaolin, barium sulfate, wollastonite, mica, titanium oxide, diatomaceous earth, hydroxyapatite and metal powder. Among these inorganic fillers, glass beads are preferable since the artificial bone model exhibiting the excellent property for cutting can be obtained.

In the process of the present invention, the method for obtaining the tomographic information of a bone is not particularly limited. Examples of the method include the magnetic resonance imaging (MRI), the X-ray computer tomography (X-ray CT) and the ultrasonic wave computer tomography (ultrasonic CT)

The laser light used for the process of the present invention is not particularly limited. Examples of the laser light include $CO_2$ laser light, YAG laser light, excimer laser light, He—Cd laser light and semiconductor excited solid laser light. Among these laser lights, $CO_2$ laser light is preferable due to the simplicity of the operation and the easiness of control. The laser light may be used singly or in combination of two or more. The time of production, the degree of binding of the sintered powder material and the porosity of the obtained artificial bone model can be adjusted by selecting the type of the laser light.

In the process of the present invention, the atmosphere under which the powder material for sintering is irradiated with the laser light is not particularly limited and may be, for example, the atmosphere of hydrogen, helium, argon, nitrogen or the air. When an inert gas is used for the atmosphere, oxidation and corrosion of the powder material for sintering can be prevented, and deformation due to excessive heating of the product by irradiation with the laser light can also be prevented.

Figure 1:
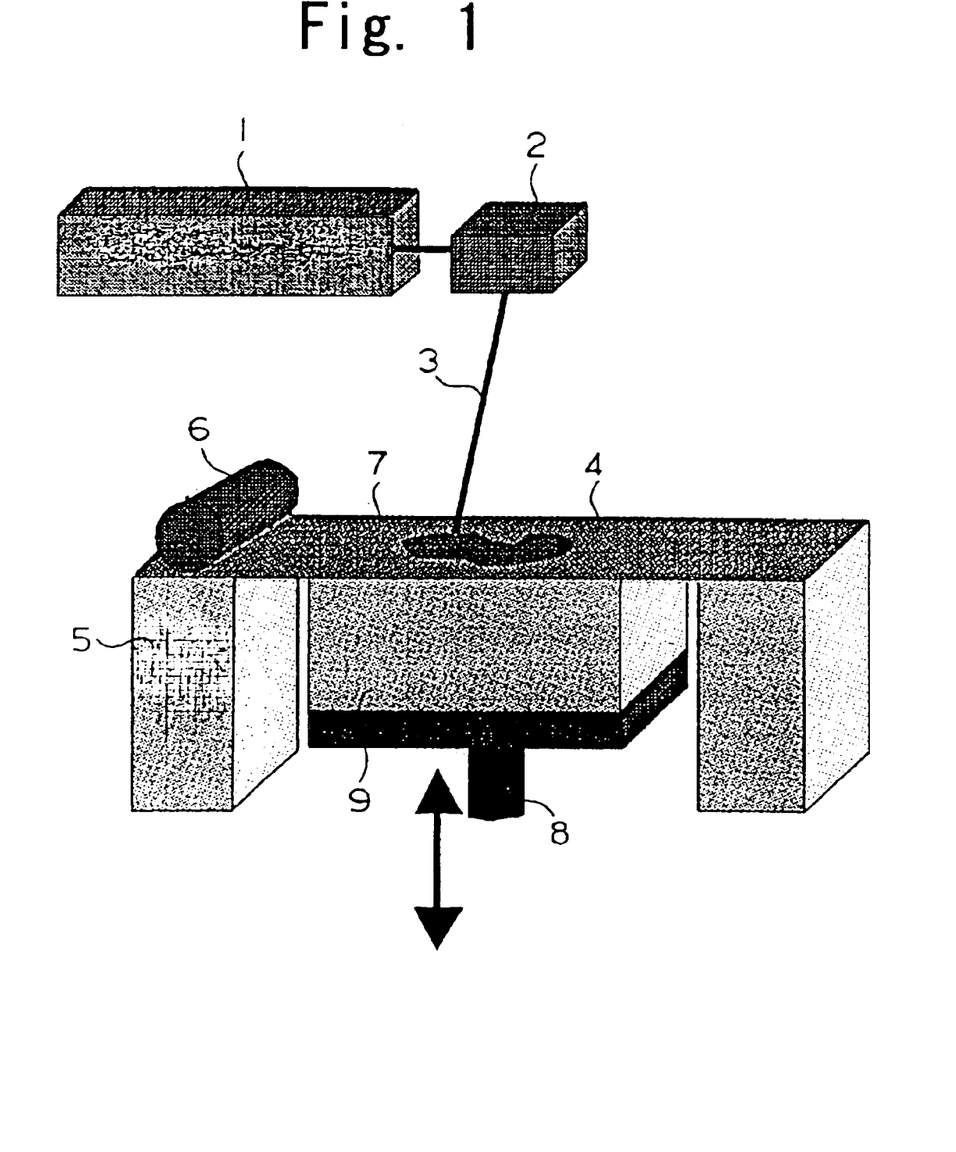
FIG. 1 shows a diagram describing an embodiment of the process of the present invention.

FIG. 1 shows a diagram describing an embodiment of the process of the present invention. In this embodiment, data of the information based on the three-dimensional CAD data are sent to a working portion from a computer control portion and the working portion starts working. The working portion is equipped with a laser 1 such as the $CO_2$ laser, the YAG laser, the excimer laser, the He—Cd laser and the semiconductor excited solid laser. A spot of the laser light 3 is focused through a galvanometer mirror 2 to form a thin beam. A powder material for sintering 5 at the surface of a powder head 4 is irradiated with the formed thin beam, and the powder material for sintering in an amount corresponding to one layer is sintered. When the irradiation is completed, a roller for supplying a powder material for sintering 6 moves in the transverse direction and supplies the powder material for sintering in an amount for one layer to the surface of the powder head. A stage 7 on which the sintered powder material is laminated is lowered by an elevator 8 by a distance of one pitch, i.e., a distance corresponding to the thickness of one layer of the supplied powder material for sintering, and the surface of the powder head is formed at the same position. In this manner, the sintering of the powder material for sintering by irradiation with the laser light, lowering of the elevator and the supply of the powder material for sintering are repeated, and the artificial bone model is completed. Since the completed artificial bone model is placed in the condition such that the model is embedded in the powder material for sintering in a part-build chamber 9 which is not sintered, the completed artificial bone model is taken out of the powder material for sintering which is not sintered. The powder material for sintering in a part-build chamber which is not sintered is recovered and used for the production of the next artificial bone model.

In accordance with the process of the present invention, since the material for the training in the medical education is prepared by directly sintering the powder material for sintering with the laser light, neither working by cutting and grinding nor preparation of an intermediate model is necessary, and the artificial bone model can be produced based on the three-dimensional CAD data alone. Therefore, the preparation of an intermediate model can be omitted, and the time for developing the materials and tools for the medical education can be decreased. Thus, the cost can be decreased.

The three-dimensional CAD data used for the selective laser sintering process are obtained by the transilluminating measurement or the contour measurement of the natural bones of a portion of the human body as the original model in accordance with a composite method comprising at least one of the magnetic resonance imaging, the X-ray computer tomography (X-ray CT), the ultrasonic wave computer tomography (ultrasonic CT) and the like. The obtained three-dimensional steric shape and the dimensional data of the natural bones of the portion of the human body by the actual measurement can be applied to the selective laser sintering process by further converting the data of the digital imaging and communications in medicine (DICOM) into the format data of the standard triangulation language (STL) of the solid type.

In accordance with the process of the present invention, not only the artificial bone model of the real size but also an accurate and precise artificial bone model having a greater size can be prepared by magnifying the real size. The magnified artificial bone model can be effectively used as a material in the lecture of anatomy in a college.

Recently, the technology of the X-ray tomography has advanced, and it is made possible that many images are produced in a short time. More accurate and more precise artificial bone models can be prepared by decreasing the pitch width of the tomographic measurement and, correspondingly, the pitch width in the selective laser sintering process, so that the resolution is enhanced.

In accordance with the process of the present invention, the artificial bone model which is completely the same as the natural bone can be prepared based on the tomographic information of the natural bone. The artificial bone model obtained in accordance with the process of the present invention exhibits the property for cutting which is closely similar to that of the natural bone. Another remarkable advantage of the present invention is that it is possible to duplicate the 3D model of radiolucent portions for example, the antrum, canal or nerves which exist inside of bone by reversing the STL data obtained based on the CT data and conducting selective laser sintering using the STL data. The method of reversing the CT data is not particularly limited. For example, it is possible to reverse the 3D-CAD data built from CT data or to reverse in a computer the standard STL data made by using the 3D-CAD data built from CT data. By using this method, it is possible to create easily the models of semicircular canal, cochlear duct and facial nerve, which is very difficult to create by the conventional method. By using this method, it is even possible to produce a model of the antrum or canal of a living human body precisely and accuratly replicating the antrum of canal in the form of solid 3D-model. The conventional process of producing such an artificial model cannot be applied for living human body. In the conventional process, the artificial model of antrum or canal has been produced only by injecting a liquid curable resin into the antrum or canal of a dead body and removing the other portion of the body than the portion of the antrum or canal by anatomizing the body after the resin has been cured.

Furthermore, it is possible to create bone models which precisely and accurately reproduce the density of bones and enables to create the bone model of, for example, osteoporosis. It is also easy to obtain a bone model exhibiting the inner structure of the bone, a bone model which is magnified or reduced from the actual dimensions or a bone model which is in a mirror image of a bone. Therefore, the educational training of younger doctors having limited experience can be conducted to improve their skill using the artificial bone model obtained in accordance with the process of the present invention in place of the natural bone. It is expected that, in the educational training in the field of the regeneration medical treatment, the training for cutting using the artificial bone model closely similar to the natural bone can provide doctors knowing well even the inner structures of natural bones.

In accordance with the process of the present invention, an artificial bone model of the portion for the operation is prepared, and the condition of the portion for the operation is observed sterically. The prepared artificial bone model is actually cut, connected and butted and, thus, the plan of the operation can be studied in detail and decided. For example, when tumor is formed in a bone, an artificial bone model including the tumor is prepared and the plan of the operation for removing the tumor can be studied. Since an artificial bone model of a cartilage can also be prepared in accordance with the process of the present invention, an artificial bone model of a larynx portion is prepared, and the plan of the operation for curing trouble in vocality can be studied. By studying the above plans in advance, the most suitable means of curing can be selected so that the load on the patient is decreased by decreasing the time for the operation, and the reliability of the operation is enhanced. Heretofore, for butting a defect of a bone, an implant material having a size greater than necessary is prepared in advance and worked during the operation to make the material fit the defect. In contrast, by studying in advance using the accurate artificial bone model prepared in accordance with the process of the present invention, the implant material in a shape close to that of the defect is prepared in advance, and the amount of working during the operation can be decreased.

By explaining the condition of the disease to the patient through demonstration of the artificial bone model of the patient prepared in accordance with the process of the present invention, a plurality of means for the examination and the cure can be presented together with the effects, the advantages, the effects after the treatment and the drawbacks of each means, and the informed consent can be obtained.

Since, unlike conventional models of the human body, the artificial bone model prepared in accordance with the present invention has not only the appearance but also the inner structures closely similar to the actual human body, the dynamic ability of a bone can be estimated to a considerable degree. Therefore, rehabilitation and moving of a patient having abnormality in a bone can be studied based on the artificial bone model prepared similarly to the actual bone, and a rational and reasonable plan can be made.

Human bone has been utilized for inventing and developing medical instruments, such as dissection drill, endoscope and operation navigator system. The bone model produced by the present invention can be used as an optimum substitute for the real bone for this purpose.

To summarize the advantages of the present invention, in accordance with the process of the present invention, the artificial bone model can three-dimensionally reproduce steric shapes of natural bones such as bones in the human body precisely and accurately. Since the artificial bone model obtained in accordance with the process of the present invention has the property for cutting closely similar to that of natural bones, the educational training of younger doctors having limited experience can be conducted to improve their skill using the artificial bone model obtained in accordance with the process of the present invention in place of the natural bone. In accordance with the process of the present invention, an artificial bone model of the portion for the operation is prepared, and the condition of the portion for the operation is observed sterically. The prepared artificial bone model is actually cut, connected and butted, and the plan of the operation can be studied in detail and decided. Thus, the reliability of the operation is enhanced. The process of the present invention can be applied to prepare artificial models of the natural bones having anatomical complexity such as temporal bone including the auditory organ of human being.

EXAMPLES

The present invention will be described more specifically with reference to examples in the following. However, the present invention is not limited to the examples.

Example 1

An artificial bone model of the auditory organ of the human being consisting of the external ear, the middle ear and the internal ear was prepared in accordance with the selective laser sintering process.

A mixture of 70% by weight of powder of nylon 11 having spherical particles having an average diameter of 58 μm and 30% by weight of glass beads having an average diameter of 60 μm was used as the powder material for sintering. An apparatus for the selective laser sintering process equipped with the 100 W carbon dioxide gas laser was used as the apparatus for the preparation of a model.

Pictures of bones in the region of the external ear to the internal ear of an adult male were taken in accordance with the X-ray computer tomography and converted into data for the preparation of a model. The obtained data were input into the apparatus for the preparation of a model. Layers of the sintered powder material were formed by sintering the material successively at a pitch of lamination of 0.10 mm, and an artificial bone model of the auditory organ of the human being was obtained.

The obtained model was evaluated by a doctor specialized in otorhinolaryngology. The duplicated model was scanned by X-ray CT. The CT showed detailed inner structure as a real bone and it was found that the obtained artificial bone model was suitable as the model of the auditory organ of the human being including ossicla auditus such as cartilago meatus acustici, malleus and incus and that the feeling obtained by cutting the artificial bone model by a drill was very close to that obtained by cutting the natural bone.

Example 2

Figure 2A:
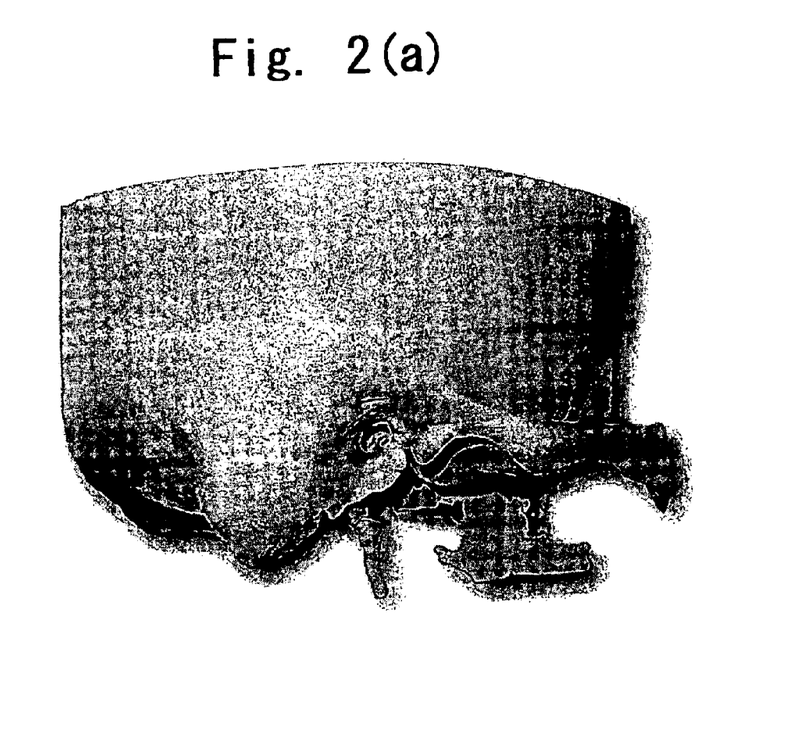
FIG. 2(a) is a photograph showing the external view of the model made from a normal subject of temporal bone manufactured by using the process of the present invention and FIG. 2(b) is a drawing by a visual field diagram of the model.
Figure 2B:
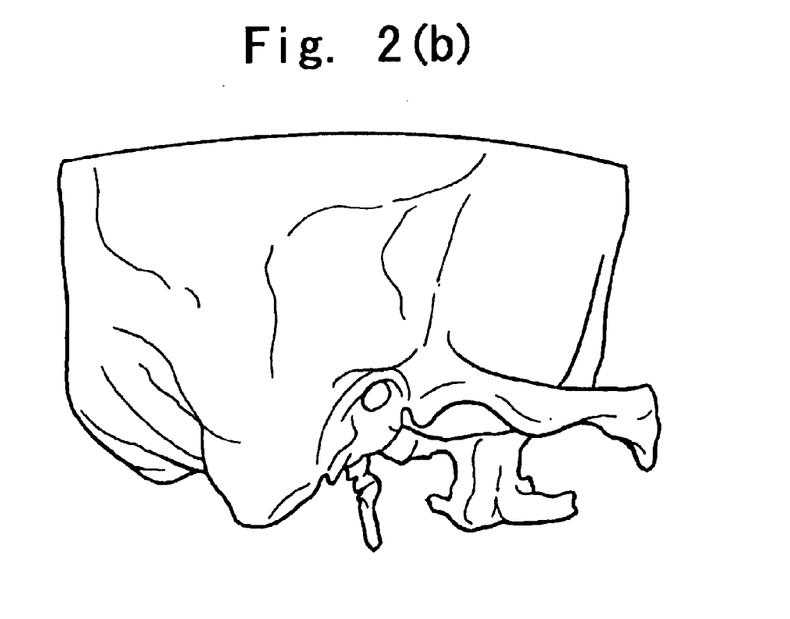
Figure 3A:
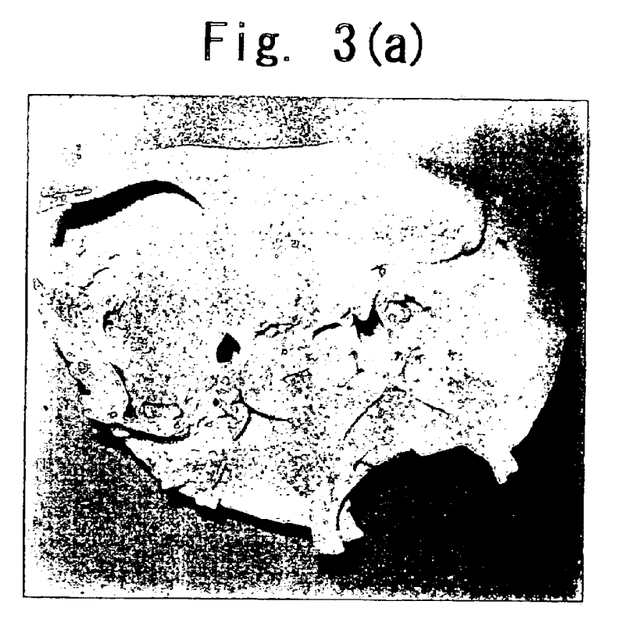
FIG. 3(a) is a photograph of a dense and hard bone model of a portion of temporal bone and FIG. 3(b) is a photograph of a loose, thin model manufactured by changing the intensity value for extracting bone shadow by using the process of the present invention.
Figure 3B:
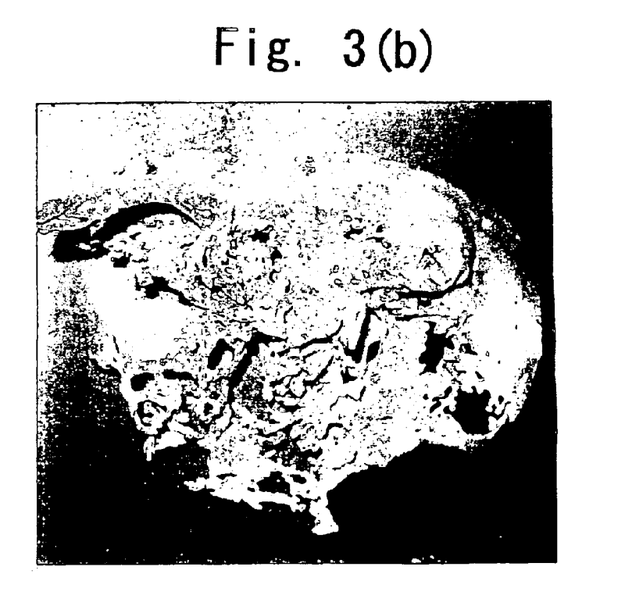
Figure 3C:
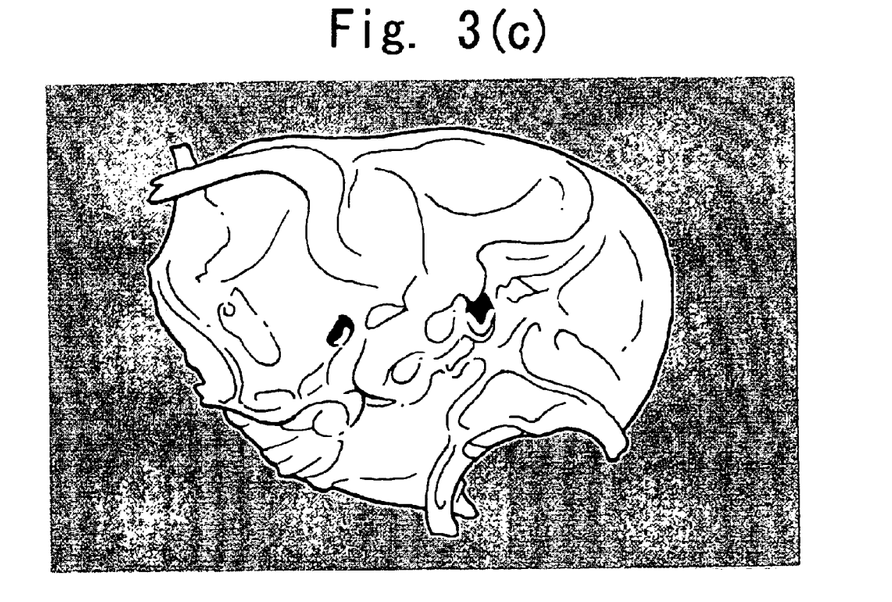
FIG. 3(c) and FIG. 3(d) are drawings by a visual field diagram of the model shown in FIG. 3(a) and FIG. 3(b), respectively.
Figure 3D:
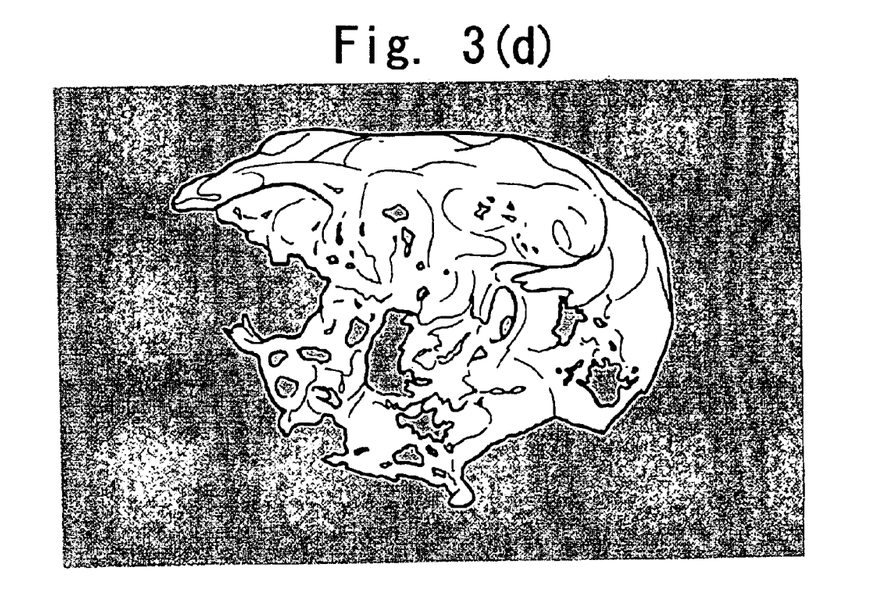
Figure 4A:
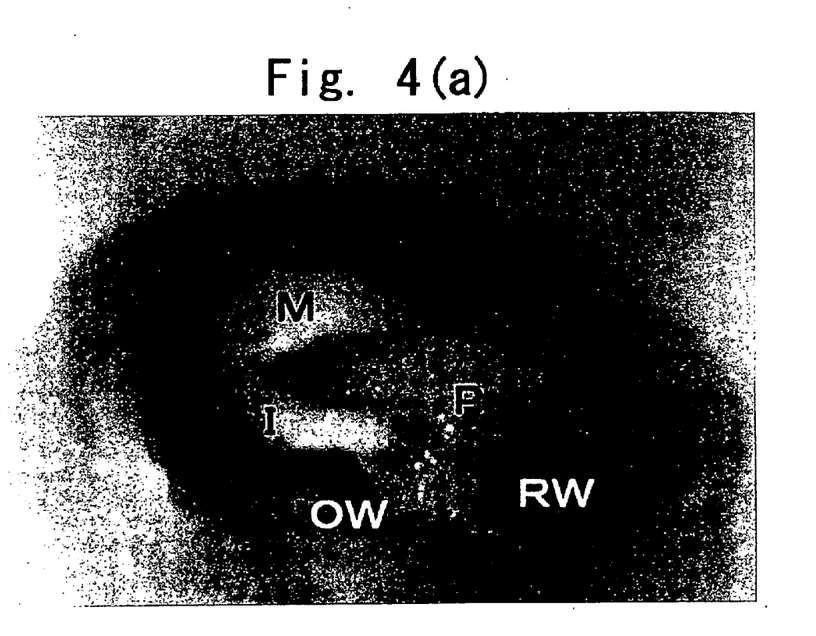
FIG. 4(a) is a photograph of a endaural view of the right side and FIG. 4(b) is a drawing by a visual field diagram of the model shown in FIG. 4(a).
Figure 4B:
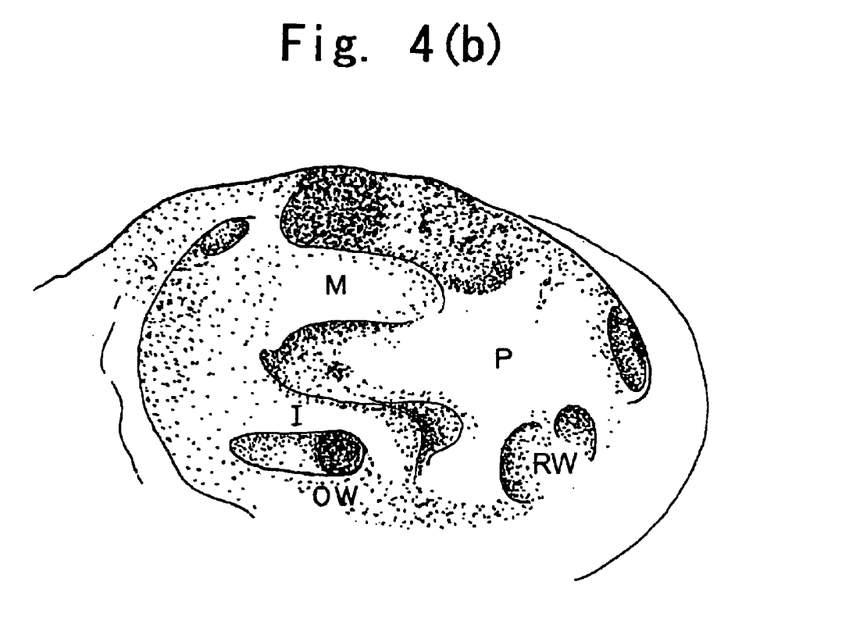
Figure 5A:
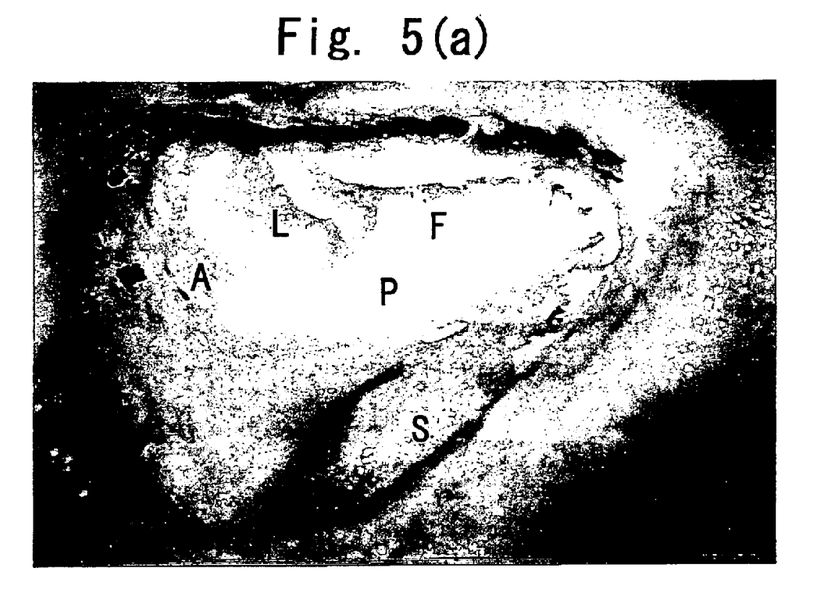
FIG. 5(a) is a photograph of a model showing drilled mastoid cavity of the right side and FIG. 5(b) is a drawing by a visual field diagram of the model shown in FIG. 5(a).
Figure 5B:
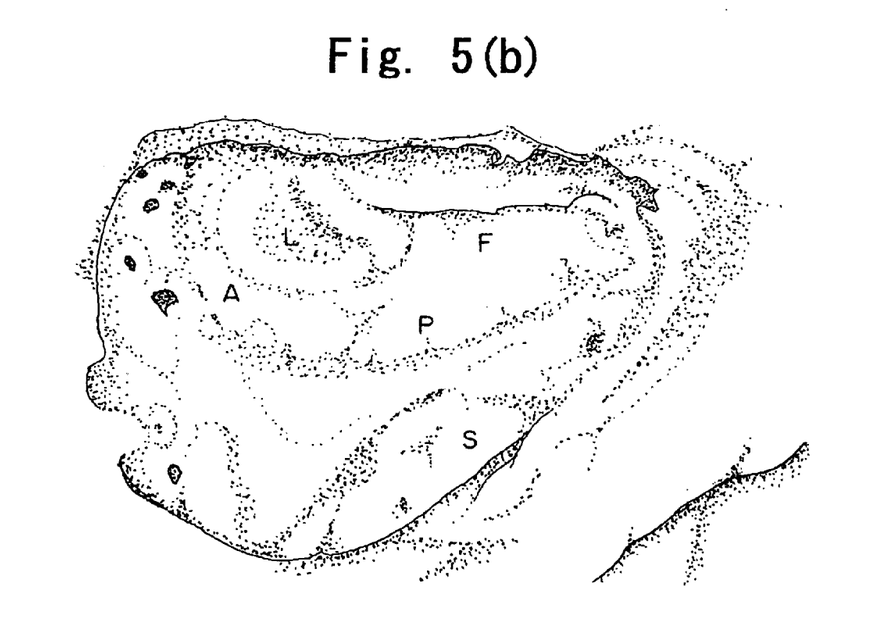

A 3-dimensionnal (3-D) model of human temporal bone was created using selective laser sintering process using a powder material for sintering used in Example 1. CT scanning raw data of a human temporal bone was taken in the horizontal plane using Asteion MDCT (Manufactured by Toshiba) with 0.5 mm of slice width, 2.5 of helical pitch and interval of image production of 0.1 mm. The data was transferred with DICOM system. The intensity value for extracting the bone shadow was determined based upon this sliced images. The derived 3-D data was converted into STL file system. The powder material for sintering was laser sintered according to the STL data extracting the bony shadow. The sintered layers were accumulated by 0.1 mm pitch. The created model was dissected under microscope using conventional surgical drill, bur, suction irrigator and instruments. The whole appearance of the model is shown in FIGS. 2(a) and 2(b). Any detailed surface structure, such as Henle's spine and tympanomastoid suture were reproduced. The density of the model changed according to the intensity value for extracting bone shadow (FIG. 3(a), FIG. 3(b), FIG. 3(c) and FIG. 3(d)). Dissection showed that the model was as hard as the real bone and was able to be shaved with bur in the same fashion as the actual surgery. Shaving produced dusts as in the real bone and the dusts was able to be removed using suction irrigator. Malleus and incus were reproduced, but stapes was not reproduced (FIG. 4(a) and FIG. 4(b)). Facial canal, round window niche, semicircular ducts and vestibule were identified (FIG. 5(a) and FIG. 5(b)). The sigmoid sinus plate appeared as bluish smooth surface by coloring the sinus inner wall blue before dissection. The ductal structures and cavity, including mastoid antrum and air cells could be easily reproduced by removing the powder which filled the ductal structures and cavity during dissection using suction irrigator and pick during drilling, because differentiation of the powder from other solid material was easy, since the powder appeared always lighter color than the other parts.

A magnified model of the human temporal bone was created for educating medical students. The model was sectioned in various planes to allow easy understanding of 3-D structures. Explaining surgery using model together with video monitoring was extremely useful to give students surgical and anatomical orientations.

Example 3

Figure 6A:
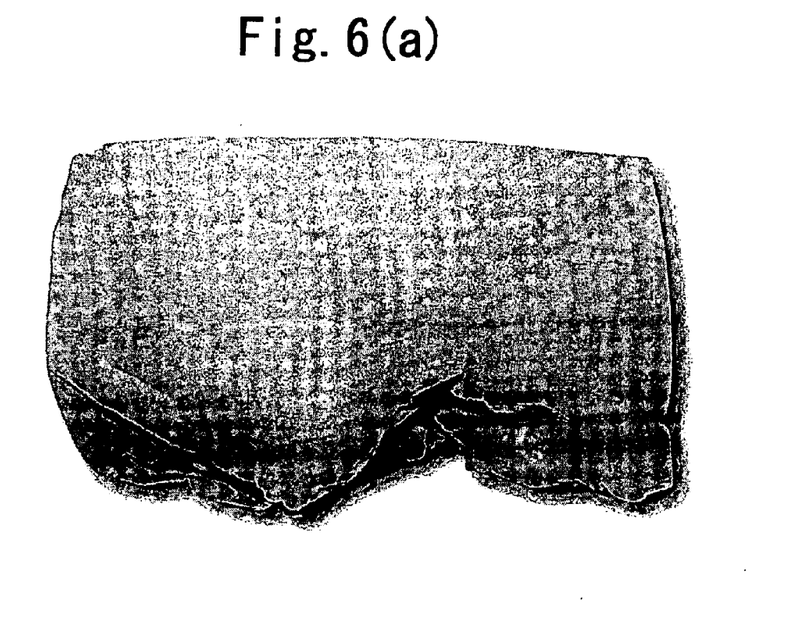
FIG. 6(a) is a photograph of a model of congenital atresia and FIG. 6(b) is a drawing by a visual field diagram of the model shown in FIG. 6(a).
Figure 6B:
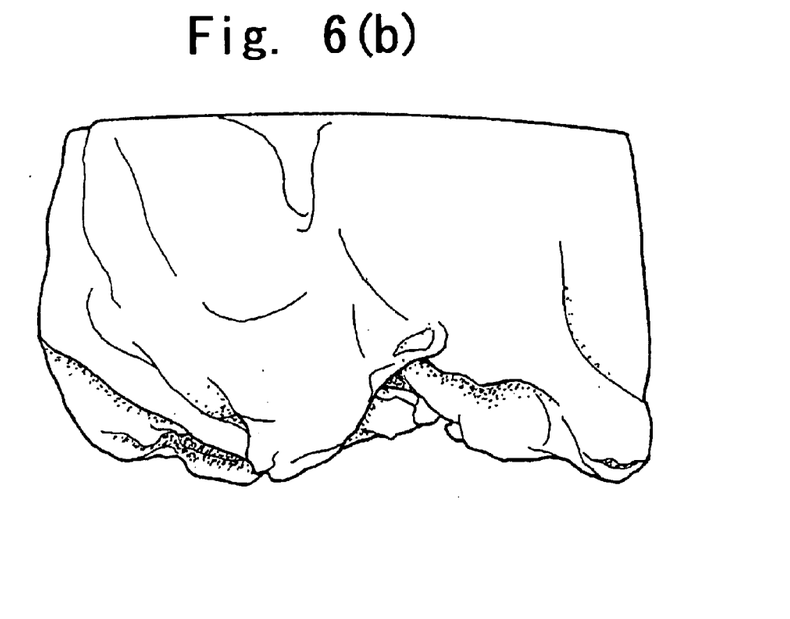

A model of congenital auditory atresia in a case of 11-year-old boy who wished to reconstruct the ear canal and ossicular chain was created in a similar method used in Example 2. The CT showed the astesia, hypoplastic middle ear cleft and ossicular anomaly. The model well reproduced the surface and inner structures (FIG. 6(a) and FIG. 6(b)). Dissection demonstrated the hypoplastic middle ear cleft and unusual location of the oval window. The oval window existed so anterioly that it was nearly hidden behind the mandibular joint space. Based on these findings, high surgical risk was expected and surgery was not dared.

Example 4

Figure 7A:
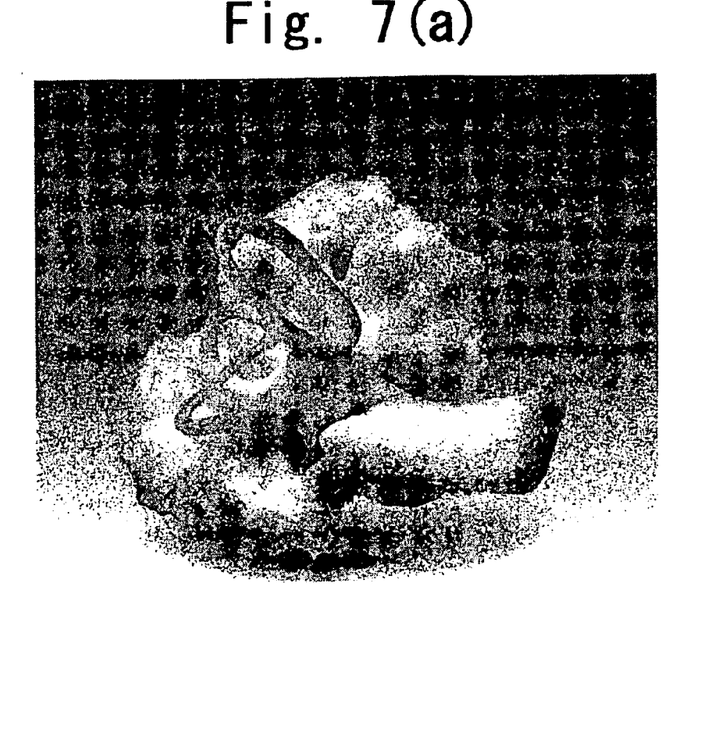
FIG. 7(a) is a photograph of a model of inner ear and internal auditory meatus manufactured by the process of the present invention and FIG. 7(b) is a drawing by a visual field diagram of the model shown in FIG. 7(a).
Figure 7B:
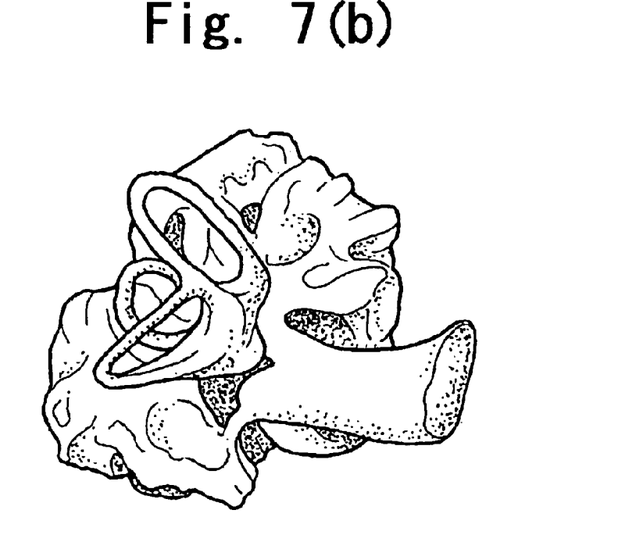

The STL data made by using the 3D-CAD data built from CT data of radiolucent areas, such as semicircular canal, cochlear duct and facial nerve obtained in Example 2 were reversed using a computer and the reversed data was input to the selective sintering machine in a manner described in Example 2. The created model represented the detailed 3-D structure of the labyrinth and facial nerve (FIG. 7(a) and FIG. 7(b)).

What is claimed is:

1. A process for producing an artificial bone model in accordance with a selective laser sintering process which comprises extending a powder material for sintering comprising 30 to 90% by weight of powder of a synthetic resin and 10 to 70% by weight of an inorganic filler to form a thin layer and irradiating a portion of the thin layer of the powder material for sintering in a shape based on tomographic information of a natural bone with laser light so that the powder material for sintering of the irradiated portion of the thin layer is sintered, the extension of the powder material for sintering to form the thin layer and the irradiation of the portion of the thin layer with laser light for sintering being conducted repeatedly, wherein the artificial bone model when cut is similar to a natural bone when cut.

2. A process according to claim 1, wherein the powder of a synthetic resin comprises fine particles having a spherical shape.

3. A process for the educational training of an individual studying a bone, the process comprising: obtaining an artificial bone model produced by the process of claim 1 and training the individual based on the artificial bone model instead of a natural bone.

4. A process for studying a plan for a surgical operation, the process comprising: obtaining an artificial bone model of a portion of a bone produced by the process of claim 1, studying the artificial bone model by cutting, connecting or butting the artificial bone model, and deciding on a plan for said operation.

5. A process according to claim 4, wherein the portion for the surgical operation is a defect of a bone and an implant material for butting a defect of the bone, which is prepared based on the artificial bone model, and is prepared prior to the surgical operation.

6. A process according to claim 1, wherein the average diameter of fine particles of the powder of a synthetic resin is in a range of 5 to 200 μm.

7. A process according to claim 1, wherein the powder of the synthetic resin is a powder of at least one resin selected from the group consisting of a nylon, a polycarbonate, a polyester, a polyacetal, polyethylene, polypropylene, polyvinyl chloride, polystyrene, polybutylene, an ABS resin, a cellulose-based resin, an acrylic resin, an epoxy resin and a fluororesin.

8. A process according to claim 7, wherein the average diameter of fine particles of the powder of a synthetic resin is in a range of 5 to 200 μm.

9. A process according to claim 7, wherein the synthetic resin is powder of a nylon resin.

10. A process according to claim 8, wherein the powder of the synthetic resin comprises fine particles having a spherical shape.

11. A process according to claim 10, wherein the inorganic filler is glass beads.

12. An artificial bone model produced by the process according to claim 11.

13. An artificial bone model according to claim 12, wherein said artificial bone is a model of a bone including a tumor or an osteoporosis.

14. An artificial bone model according to claim 12, wherein said artificial bone model is a model of a portion of a larynx.

15. A process according to claim 11 producing an artificial bone model of radiolucent areas in human bone, wherein the portion of the thin layer irradiated with the laser light is in a shaped based on CT data of the area from the tomographic information of a natural bone that has been reversed.

16. An artificial bone model produced by the process according to claim 15.

17. A process according to claim 15, wherein the reversed CT data corresponds to a radiolucent area inside the natural bone, said area being selected from the group consisting of an antrum, a canal and a nerve.

18. A process according to claim 17, wherein the radiolucent area inside the natural bone is an area selected from the group consisting of a semicircular canal, a cochlear duct and a facial nerve.

19. An artificial bone model according to claim 12, wherein said artificial bone model is selected from the group consisting of a bone model which three-dimensionally reproduces steric shapes of a natural bone and has a real size; a bone model which is magnified or reduced from the actual dimensions of a natural bone; a bone model which is a mirror image of a natural bone; and a bone model which precisely and accurately reproduces the density of a natural bone.

20. A process according to claim 1, wherein the powder of the synthetic resin is powder of a nylon resin.

21. A process according to claim 1, wherein the inorganic filler is glass beads.

22. A process according to claim 1 for producing an artificial bone model of radiolucent areas in human bone, wherein the portion of the thin layer irradiated with the laser light is in a shape based on CT data of the area from the tomographic information of a natural bone that has been reversed.

23. An artificial bone model produced by the process according to claim 1.

24. An artificial bone model produced by the process according to claim 22.

* * * * *

UNITED STATES PATENT AND TRADEMARK OFFICE
CERTIFICATE OF CORRECTION

| | | |
|---|---|---|
| PATENT NO. | : 6,932,610 B2 | Page 1 of 1 |
| APPLICATION NO. | : 10/726305 | |
| DATED | : August 23, 2005 | |
| INVENTOR(S) | : Ono et al. | |

It is certified that error appears in the above-identified patent and that said Letters Patent is hereby corrected as shown below:

Column 11, line 54 (Claim 9): delete "claim 7" and insert -- claim 8 --.

Column 12, line 14 (Claim 15): after "claim 11" insert -- for --.

Signed and Sealed this

Fifth Day of January, 2010

David J. Kappos
*Director of the United States Patent and Trademark Office*